(12) United States Patent
Fredrickson et al.

(10) Patent No.: US 8,277,867 B2
(45) Date of Patent: Oct. 2, 2012

(54) MICRODROP ABLUMENAL COATING SYSTEM AND METHOD

(75) Inventors: Gerald Fredrickson, Westford, MA (US); Bill Dorogy, Newburyport, MA (US); Todd Robida, Southbridge, MA (US); Paul Sojka, West Lafayette, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1024 days.

(21) Appl. No.: 12/208,789

(22) Filed: Sep. 11, 2008

(65) Prior Publication Data
US 2009/0074943 A1 Mar. 19, 2009

Related U.S. Application Data

(60) Provisional application No. 60/972,297, filed on Sep. 14, 2007.

(51) Int. Cl.
*B05D 1/04* (2006.01)
*B05B 5/035* (2006.01)
*B05C 11/02* (2006.01)

(52) U.S. Cl. .................... 427/2.1; 118/624; 118/708

(58) Field of Classification Search .................. 427/2.1; 118/624, 708
See application file for complete search history.

(56) References Cited

U.S. PATENT DOCUMENTS

| | | | |
|---|---|---|---|
| 6,669,980 B2 | 12/2003 | Hansen | |
| 6,682,771 B2 | 1/2004 | Zhong et al. | |
| 6,743,463 B2 | 6/2004 | Weber et al. | |
| 6,746,869 B2 | 6/2004 | Pui et al. | |
| 6,861,088 B2 | 3/2005 | Weber et al. | |
| 7,208,190 B2 | 4/2007 | Verlee et al. | |
| 7,247,338 B2 | 7/2007 | Pui et al. | |
| 7,449,210 B2 | 11/2008 | Malik et al. | |
| 7,455,875 B2 | 11/2008 | Weber et al. | |
| 2005/0058768 A1 | 3/2005 | Teichman | |
| 2006/0177573 A1 | 8/2006 | Pui et al. | |
| 2006/0217801 A1 | 9/2006 | Rosenthal | |
| 2007/0077435 A1 | 4/2007 | Schachter et al. | |
| 2007/0231457 A1 | 10/2007 | Pham et al. | |
| 2007/0233270 A1 | 10/2007 | Weber et al. | |

FOREIGN PATENT DOCUMENTS

| | | | |
|---|---|---|---|
| DE | 10153708 | | 5/2003 |
| WO | 8910566 | | 11/1989 |
| WO | 2004047882 | | 6/2004 |
| WO | WO 2004/047882 | * | 6/2004 |
| WO | 2007089881 | | 8/2007 |
| WO | 2007089883 | | 8/2007 |
| WO | WO 2007/089883 | * | 8/2007 |

OTHER PUBLICATIONS

Eric Lee, Microdop Generation, Methods of Generating Monodisperse Microdrops, CRC Press 2003, pp. 15-29.

* cited by examiner

*Primary Examiner* — Robert D. Harlan
(74) *Attorney, Agent, or Firm* — Vidas, Arrett & Steinkraus, P.A.

(57) ABSTRACT

Systems and methods for coating medical devices are provided that allow for relatively precise control over the deposition area and coating uniformity with improved efficiency. A microdrop source is used to provide a flow of coating microdrops. A charging electrode disposed near the outlet of the coating source gives each microdrop an electrostatic charge. As the microdrop travels toward the medical device to be coated, a control electrode alters the trajectory of the microdrop. The invention can include a scanner to scan or image the medical device as the coating is applied and a control system to adjust parameters of the deposition process based on information provided by the scanner.

22 Claims, 3 Drawing Sheets

MICRODROP ABLUMENAL COATING SYSTEM AND METHOD

CROSS REFERENCE TO RELATED APPLICATION

The present application claims priority to U.S. provisional application Ser. No. 60/972,297 filed Sep. 14, 2007, the disclosure of which is incorporated herein by reference in its entirety.

FIELD OF THE INVENTION

The present invention relates to coating medical devices, such as stents. More specifically, the present invention is directed to the field of coating a medical device using charged microdrops of a coating material.

BACKGROUND

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systematic side effects. Such localized delivery of therapeutic agents has been proposed or achieved using medical implants which both support a lumen within a patient's body and place appropriate coatings containing absorbable therapeutic agents at the implant location.

The delivery of expandable stents is a specific example of a medical procedure that may involve the deployment of coated implants. Expandable stents are tube-like medical devices, typically made of stainless steel, Tantalum, Platinum, or Nitinol alloys, designed to be placed within the inner walls of a lumen within the body of a patient. These stents are typically maneuvered to a desired location within a lumen of the patient's body and then expanded to provide internal support for the lumen. The stents may be self-expanding or, alternatively, may require external forces to expand them, such as by inflating a balloon attached to the distal end of the stent delivery catheter.

The process of applying a coating onto a stent or other medical device may be accomplished in a variety of ways, including, for example, spraying the coating substance onto the device using conventional gas-assist or ultrasonic atomization, conventional electrospraying, and electrostatic fluid deposition, i.e., applying an electrical potential difference between a coating material and a target device to be coated, causing the coating material to be discharged from the dispensing point and attracted toward the target by an electric field.

Common to these processes is the need to apply and dry the coating in a manner to insure that an intact, encapsulated and robust coating of the desired thickness is formed on the stent. Equally important is the need to control coating uniformity and quality (on the outside coated surface of a substrate, any radial, side-wall surface of a latticed substrate, and/or inner surfaces of a substrate), coating deposition efficiency, and coating droplet or particle size distribution and concentration.

Conventional gas-assist coating methods, such as coating applications utilizing a gas atomization nozzle, have been used to coat medical devices. However, conventional gas-assist coating methods have shown intrinsic problems in adequately controlling coating uniformity and coating quality through the generated coating droplet size distribution and resulting drying time of the coating film, which can affect the kinetic drug release rate in coatings with embedded drug particles. In addition, conventional gas-assist methods delivered by high-velocity gas streams may have low deposition efficiencies with either partial or incomplete deposition or excessive overspraying. In many systems, generally only about 5% of the coating material or solution that is sprayed from a gas atomization nozzle is deposited on a medical device. The remaining 95% of the coating solution is lost in excessive overspraying and is therefore wasted. Deposition efficiencies have become more important as coating materials have increased in cost, and product processing throughput has become limited by the coating efficiency rate.

Conventional electrospraying and electrostatic methods have also been used to coat medical devices. Conventional electrospraying methods can have relatively high deposition efficiency rates, and can adequately control coating uniformity and droplet sizing for electrically conductive coating materials or solutions. However, controlling droplet sizes and maintaining a stable or robust spray coating process within the well-known "cone-jet" mode can become more difficult with coating solutions having a low electrical conductivity. Conventional electrospraying methods use metal capillary tubes which are electrically conductive and either rely on intrinsic charge carriers or dissociation of ions in a conductive solution to achieve the desirable coating performance. As a result, conventional electrospraying methods require a coating material or solution with adequate electrical conductivity, which can be achieved through mixture design or conductivity additives; conventional electrospraying methods may thus be incompatible with insulative solutions. Conventional methods such as gas-assist and electrospraying may also prevent precise control over the trajectory or specific deposition location of the material to be deposited.

SUMMARY OF THE INVENTION

The present invention provides systems and methods for coating medical devices that allow for relatively precise control over the deposition area and coating uniformity with improved efficiency. The invention may allow for specific areas of a medical device, such as individual struts of a stent, to be accurately and efficiently coated.

In an embodiment of the invention, a microdrop source is used to provide microdrops of a coating material. Exemplary microdrop sources include ink jet, thermal ink jet, piezoelectric direct pressure pulse, acoustically disrupted continuous fluid jet, and focused acoustic beam ejection devices. Other microdrop generating systems may be used, though it is preferred that the microdrop source be capable of providing a constant frequency of microdrops. Microdrops of coating material created by the microdrop source are ejected toward a medical device to be coated, such as a stent.

As each microdrop is ejected from the microdrop source toward the medical device to be coated, a charging electrode disposed near the outlet of the coating source may give each microdrop an electrostatic charge, such as by induction charging. The charging electrode may be, for example, a ring electrode through which the microdrops travel, or an electrode with a pointed tip placed near the coating source outlet. Other charging electrodes may be used.

As the microdrop travels toward the medical device to be coated, a control electrode may be used to control the trajectory of the microdrop, and ultimately the location on the medical device at which the microdrop is deposited. For example, a microdrop may be given a positive charge by the charging electrode. If a positively-charged control electrode is positioned adjacent to the trajectory of the microdrop, the charge will be accelerated away from the control electrode. A similarly-positioned negatively-charged control electrode will cause a positively-charge microdrop to accelerate toward the control electrode. By positioning the control electrode at various points relative to the medical device or adjusting the charge on or voltage across the control electrode, an operator of the device may control the location at which the microdrop ultimately deposits on the medical device. In an embodiment, multiple electrodes may be used to provide more precise control over the trajectory of each microdrop. In another embodiment, magnets or electromagnets may be used to generate a magnetic field between the microdrop source and the medical device. The magnetic field can then be used to control the path along which the charged microdrop moves.

In an embodiment, a scanner may be used to scan or image the medical device as the coating is applied. For example, the scanner may comprise an imaging camera and/or a process monitoring camera. The scanner may examine the medical device to determine if the microdrop source and electrodes are positioned over a portion of the device to be coated. A control system may then use this information to position the microdrop source and electrodes, and to manipulate the electric field created by the control electrodes. Hence coating may be deposited on desired portions of the medical device.

In an embodiment, a waste tray may be used. In such an embodiment, the microdrop source may produce a steady, constant-frequency series of coating microdrops. When a scanner indicates that the microdrop source and electrodes are not positioned over a portion of the device that is to be coated, or that the microdrop path cannot be altered sufficiently to direct the microdrop onto a desired area of the medical device, the electric field created by the control electrodes may be adjusted to direct generated microdrops into the waste tray. This may allow the system to coat only desired portions of the medical device while maintaining a steady flow of microdrops. Coating collected in the waste tray may be reused, such as by returning the collected coating to the microdrop source, or it may be discarded.

DETAILED DESCRIPTION

Figure 1:
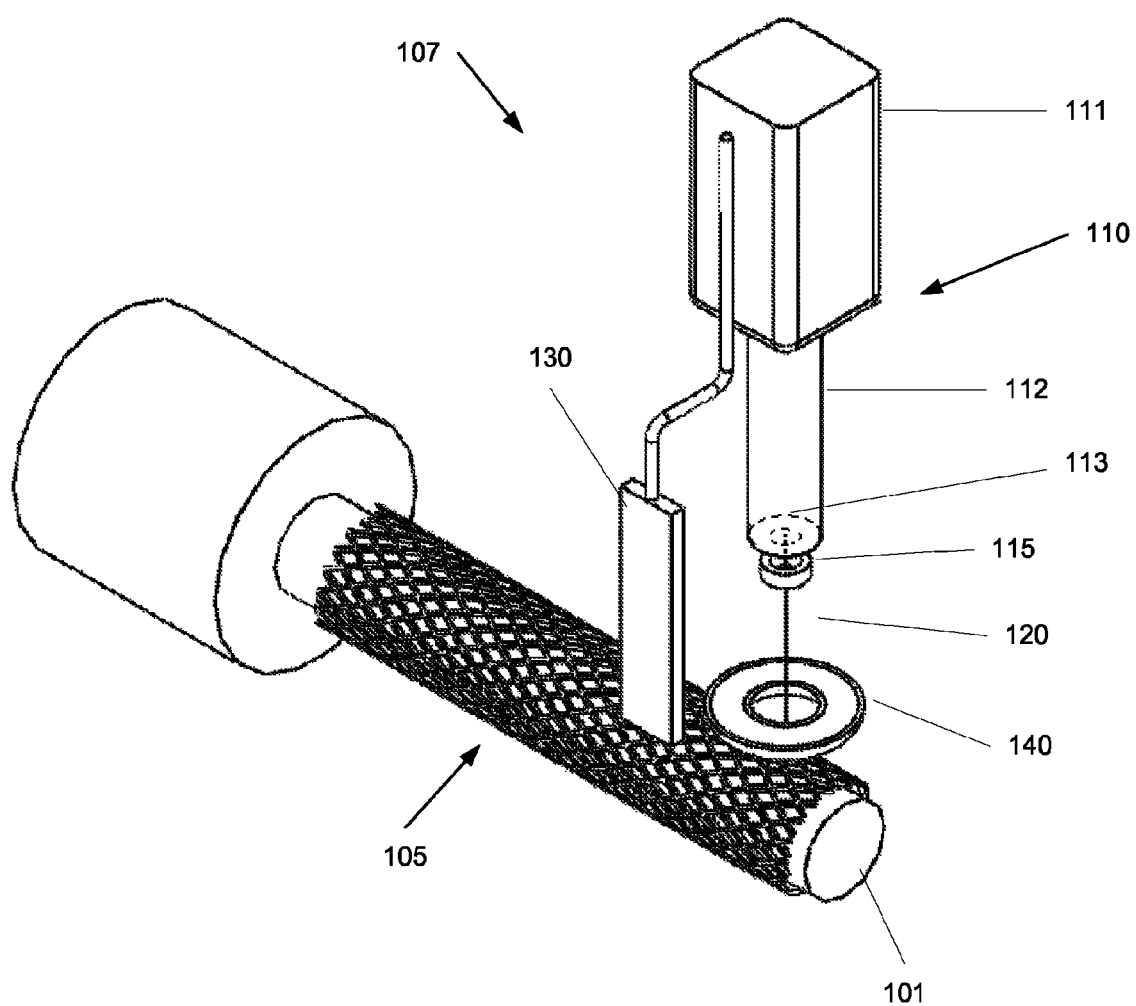
FIG. 1 shows a perspective view of a system for coating a medical device according to an embodiment of the present invention.

FIG. 1 shows an embodiment of the invention. A deposition system 107 is used to deposit a coating onto a medical device 105, such as a stent. The medical device 105 is positioned on a support 101. For example, when a stent it to be coated it may be placed on a cylindrical support. The support 101 and the deposition system 107 may be positionable relative to each other. For example, in the system shown in FIG. 1 the support 101 may be rotated by an operator or a control system, and the deposition system 107 may be translated along the length of the medical device 105. In another embodiment, the medical device 105 may be held on a stationary support 101 while the deposition system 107 rotates around the device, translates along its length, or both. In yet another embodiment, the deposition system may be stationary while the support 101 may rotate around the longitudinal axis of the support 101 and/or translate in a direction along its axis. Other configurations may be used. For example, the support 101 may rotate around the longitudinal axis of the support, and the deposition system 107 may translate along an axis of the medical device 105. It is preferred that the deposition system and medical device support be positionable such that the deposition system may place coating on each desired surface of the medical device. In another embodiment, multiple deposition systems 107 may be used. For example, a plurality of deposition systems may be positioned along the diameter of the medical device 105 to increase production throughput.

The deposition system may include a microdrop source 110, a charging electrode 115, one or more control electrodes 130, and a waste tray 140. Exemplary microdrop sources include acoustically disrupted continuous fluid jets, thermal inkjets, piezoelectric direct pressure pulse jets, and focused acoustic beam jets. Other types of microdrop sources may be used. Microdrop sources are described, for example, in Eric Lee, *Microdrop Generation*, CRC Press 2003, pp. 15-29, which is incorporated herein by reference. Such sources may be advantageous as they allow for control over the size of microdrops created and the charge that can be placed on the microdrops. Although these sources may be referred to as, for example, "ink jet" technology, it will be understood that in the present invention the various jets are used to deposit a coating as opposed to a dye-containing ink. Such a coating may contain a therapeutic agent. Exemplary coatings and further information regarding their composition are given below.

Generally, the microdrop source 110 may include a reservoir 111 to store coating to be applied to the medical device. For example, the reservoir 111 may store a solution having a dissolved polymer and therapeutic agent. The solution may be applied to the medical device in liquid form, and later dried to form a polymer coating. The microdrop source may also include a nozzle 112, which is in fluid communication with reservoir 111, to accelerate microdrops to a velocity sufficient to reach the medical device in a desired amount of time. The nozzle 112 comprises an outlet 113, through which microdrops of coating material may be ejected from the microdrop source 110 toward medical device 105. Other configurations for the microdrop source may be used, such as those described above.

It is preferred that the microdrop source 110 eject a relatively constant frequency of coating microdrops 120. A series of ejected microdrops may be referred to as a stream or flow of microdrops. When the microdrops are ejected from the source 110, they travel from the source to the medical device 105. The microdrops may be given an electric charge by a charging electrode 115. The charging electrode 115 may be a ring electrode, as shown in FIG. 1, or it may be a pointed electrode disposed near the outlet of the source. For example, a pointed electrode may be an elongated electrode or a conical electrode with the pointed or sharp end positioned proximally to the nozzle outlet 113. Other charging electrode configurations are possible. For example, a probe electrode 340 used to charge coating material in a reservoir is described below with respect to FIG. 3.

To produce an electric charge on the microdrops, the charging electrode is given an electric charge. For example, in the configuration illustrated in FIG. 1 a charge is induced on each microdrop as the microdrop travels past the charging electrode due to its proximity to the charging electrode 115. This process may be referred to as electrostatic charging or induction charging. In the case of direct charging configurations, such as the probe electrode illustrated in FIG. 3, the charging electrode may directly transfer electric charge to the coating stored in reservoir 111. The charge may be transferred before or after microdrops have been formed by the microdrop source.

As the microdrops travel toward the medical device, a control electrode 130 may be used to alter the trajectory of the microdrops. When the control electrode is given an electric charge, it creates an electric field in the region through which the microdrops travel. The strength and direction of the electric field is determined by the polarity and strength of the charge placed on the control electrode. The electric field then affects the trajectory of each microdrop by exerting a force on the microdrop. For example, if a microdrop is given a positive charge, a positively-charged control electrode may be used to accelerate the microdrop away from the control electrode, and thus alter the trajectory of the microdrop in a direction away from the control electrode. Alternatively, a negatively-charged control electrode may be used to adjust the trajectory of a positively-charged microdrop toward the control electrode. The control electrode 130 may be any shape or configuration. For example, plates, rods, or spheres may be used to allow for simple construction, while more complicated electrode shapes may be used to provide more uniform fields.

Figure 2:
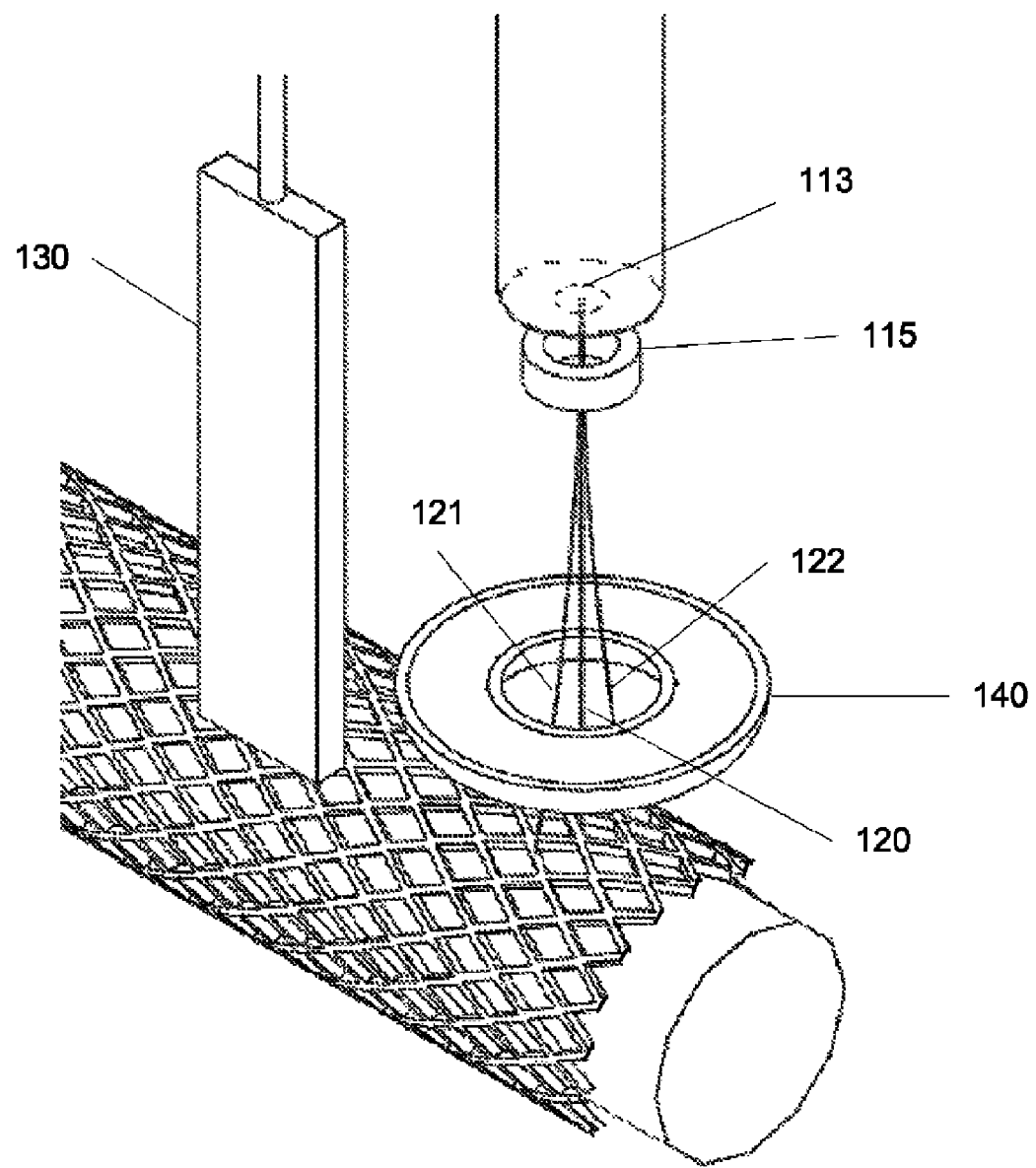
FIG. 2 shows an expanded perspective view of a system for coating a medical device according to an embodiment of the present invention.

FIG. 2 shows an enlarged view of a control electrode positioned to alter the trajectory of microdrops ejected from a microdrop source. As microdrops are ejected from the source, they may pass through a charging electrode 115 and acquire an electric charge. An electric field (not shown) created by the control electrode 130 may then alter the trajectory of the microdrops. The microdrops may therefore be directed along various trajectories 121, 122. For example, a positively-charged control electrode may result in positively-charged microdrops following a trajectory 122 away from the control electrode 122. Alternatively, a negatively-charged control electrode may attract positively-charged microdrops, resulting in a trajectory 121 toward the control electrode. Trajectories other than the specific examples shown in FIG. 2 may also be achieved. If a greater charge is given to the control electrode 130, the change in the microdrop trajectory may be greater. Generally, the electrical force $\vec{F_E}$ on a charged microdrop may be modeled as $\vec{F_E}=q\vec{E}$, where $\vec{E}$ is the electric field generated by the control electrode and q is the charge of the microdrop. Since the force on each microdrop is proportional to both the electric field and the charge on the particle, embodiments of the invention may allow for the use of coating materials that comprise, for example, proteins that are sensitive to or easily damaged when a relatively large charge is placed on microdrops of the material. In the present invention, these materials may be used, for example, by placing a lower, conservative charge on each microdrop, and adjusting the strength of the electric field to compensate for the lower charge. Further, the invention allows for the use of microdrops with enhanced stability. Some coating materials may be sensitive to electric charge because when a charge is applied to the microdrop, it localizes on the surface of the microdrop. If the charge is sufficiently high the resulting repulsion may overcome the surface tension of the microdrop and result in destruction of the microdrop and/or damage to the coating material. In some materials, a relatively high electric charge may also alter the tertiary structure of the material, which may undesirably affect its properties.

Referring again to FIGS. 1-2, the deposition system 107 may be positioned relative to the medical device 105, such that microdrops of a coating material may be deposited on desired areas of the device. The control electrode 130 may also be used as previously described to more precisely direct coating microdrops onto the device. For example, if a stent is to be coated the microdrop source may be positioned over a general region of the stent to be coated. As microdrops are ejected, the control electrode 130 may be used to alter the trajectory of the ejected microdrops such that the microdrops are deposited on struts of the stent. When there are no areas to be coated within reach of the microdrop stream, i.e., the microdrop trajectory cannot be altered enough to direct microdrops at a desired area of the medical device, the deposition system and/or medical device may be repositioned.

In another embodiment, the microdrop trajectories may be altered in a manner that permits coating of specific areas or regions of the medical device. For example, if the medical device to be coated is a stent it may be desirable to deposit coating on only the outer surfaces of the stent struts, on the outer surface and sides of the struts, or only on the sides of the struts. Using the present invention, coating may be directed to only those regions on which coating is desired. In some cases, such as where a coating is desired on the surface and sides of struts, the microdrop trajectories may be altered such that they are deposited on both the surface and sides of the struts. If, for example, only the sides are to be coated, the deposition system 107 may be positioned and the microdrop trajectories adjusted such that coating is applied only to the sides of the struts.

In another embodiment, when there are no areas within reach of the microdrop stream, the microdrop stream may also be directed into a waste tray 140. This may prevent overspraying of the device, and may allow recapture of unused coating. The unused coating collected in the waste tray 140 can be discarded, reclaimed for later use, or returned to the reservoir 111 for reuse. The waste tray 140 may be attached to the deposition system 107, such that it is always within range of the trajectories through which ejected microdrops may travel. Use of a waste tray also allows for more efficient operation of the microdrop source, since the source may be run continuously (e.g., without starting and stopping the deposition system 107 or repositioning the medical device 105 based on whether a portion of the medical device to be coated is in range).

Figure 3:
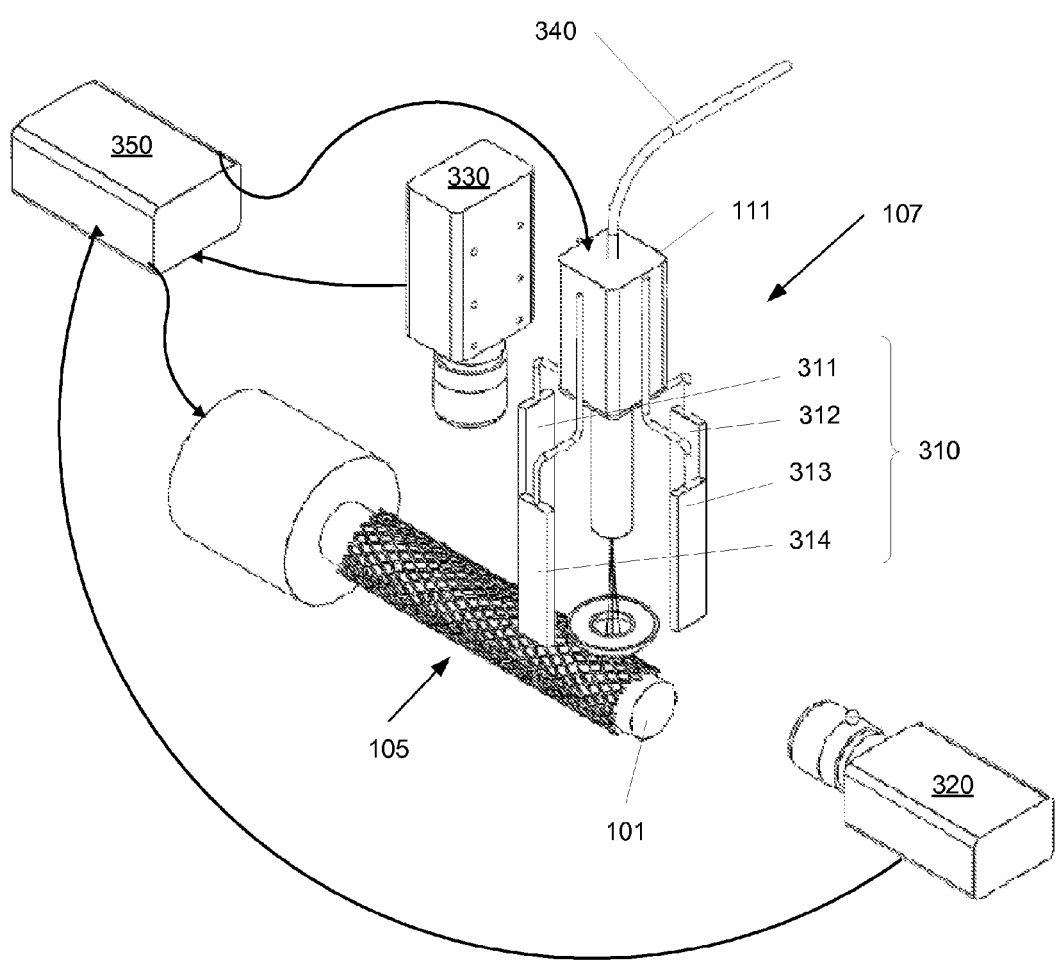
FIG. 3 shows a perspective view of a system for coating a medical device according to another embodiment of the present invention.

In an embodiment, an array of electrodes may be used as the control electrode to allow more precise control over the microdrop trajectory. For example, several electrodes may be positioned at regular intervals around the region through which the microdrops travel. FIG. 3 shows an example of a control electrode comprising an electrode array 310. In an embodiment, each electrode or pair of electrodes may be controlled individually. By varying the strength and polarity of the electrodes in the array, the generated electric field and hence the change in the microdrop trajectory may be precisely controlled. By controlling each electrode in the electrode array 310, complex electric fields may be produced, allowing for greater control over the path traveled by the microdrops.

For example, an electrode array 310 may include four electrodes 311, 312, 313, 314. One electrode 311 may be positively charged, and the electrode 313 disposed on the opposite side of the microdrop stream may be negatively charged (i.e., a voltage may be applied across the pair of electrodes), creating an electric field between the two electrodes 311, 313. By varying the charge on the electrodes 311, 313, the trajectory of the microdrops may be altered. If the trajectory of the microdrops is to be altered in a direction perpendicular to the electric field formed by the electrodes 311, 313, the charge may be removed from the electrodes 311, 313 and the other electrodes 312, 314 in the array may be given a charge. For example, one electrode 312 may be given a positive charge and the other electrode 314 may be given a negative charge, creating an electric field between the electrodes 312, 314 in a direction perpendicular to the field created between the first pair of electrodes 311, 313. Other arrangements of electrodes in the electrode array 310 may be used. One or all of the electrodes may be electrically charged by application of constant or variable voltages.

In an embodiment, a scanner or scanning system may be used to scan or image the medical device as the coating is applied. The scanner may comprise a closed-circuit camera and monitor system, with an automated vision or image recognition system. Other scanners may be used, such as laser-based systems, infra-red scanning systems, height sensors (e.g., to monitor device and/or coating deposition thickness), and other imaging and scanning systems known in the art. For example, the scanner may comprise an imaging camera 330 and/or a process monitoring camera 320, as shown in FIG. 3. The scanner may examine the medical device and monitor the coating process to determine if the microdrop source and electrodes are positioned over a portion of the device to be coated. A control system may then use this information to position or reposition and adjust the relative positions of the medical device and the deposition system, and/or to manipulate the electric field created by the control electrodes. Hence coating may be deposited on desired portions of the medical device.

The scanning system may also allow for real-time scanning of the medical device. In an embodiment, the medical device is scanned and the surface of the device plotted while coating material is deposited on the device. If the medical device 105 is moved unintentionally, such as by shifting of the device 105 on the support 101, the scanning system can adjust for the movement of the medical device without requiring the entire device to be re-scanned. This may allow for the system to adjust to such shifts in device positioning without substantial overspraying of the device or waste of the coating.

When a scanner or scanning system is used, it may be connected to a control system 350 to allow for real-time control of coating deposition. As microdrops are ejected from the deposition system 107, the scanner may monitor deposition of the microdrops and positioning of the deposition system 107 relative to the medical device 105, allowing for automated or semi-automated coating. As the scanner images the surface of the medical device to be coated, a "plot" of the medical device may be provided to the control system. Information about the deposition process, such as the thickness of any coating that has been deposited, may also be provided to the control system. The control system 350 may then move the deposition system, the support, or both, and/or adjust the electric field generated by the control electrode to provide a coating to desired areas of the medical device. As shown in FIG. 3, the control system may be in communication with the scanning system 320 and 330, the medical device support 101, and/or the deposition system 107. The scanning may be done while the medical device and deposition system are in relative motion. As previously described, if the deposition system is placed such that there is no desired area of the medical device that can be coated, the microdrop flow may be directed into a waste tray. The scanning system may allow for real-time control of coating deposition with a minimum of starting and stopping of the deposition system; this control may enhance consistency of microdrop generation frequency. A more consistent frequency of drop generation can reduce clogging of the outlet of the microdrop source, and improve alignment of the microdrops and consistency in microdrop sizing, which may result in enhanced coating quality and consistency.

Other configurations of the invention are further illustrated in FIG. 3. For example, a probe electrode 340 may be used to create a charge on the microdrops. The probe electrode 340 may be placed in electrical contact with coating material stored in the reservoir 111 to generate an electrical charge on the coating material. The coating is thus charged prior to being ejected from the deposition system 107. The charged microdrops may then be manipulated using the control electrode 310 as previously described.

In another embodiment, the control electrode 310 may generate a magnetic field. With respect to such an embodiment, a "control electrode" as used herein may refer to a device capable of generating a magnetic field. For example, an electrode array 310 may include electromagnets. In this embodiment, microdrops are given an electric charge using any of the previously-described configurations. The control electrode 310 may generate a magnetic field in the region between the deposition system 107 and the medical device 105. As the charged microdrops travel through this region, their trajectories are altered by the magnetic field. By controlling the magnetic field generated by the control electrode 310, the trajectories of ejected microdrops may be controlled. The force $\vec{F_B}$ on a charged microdrop may be modeled as $\vec{F_E} = q\vec{v} \otimes \vec{B}$, where $\vec{B}$ is the magnetic field generated by the control electrode, $\vec{v}$ is the velocity of the microdrop and $\otimes$ is the vector cross product. The acceleration on a charged microdrop is therefore in a direction perpendicular to both the velocity of the microdrop and the magnetic field generated by the control electrode.

The therapeutic agent in a coating of a medical device of the present invention may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc-oncogene; anti-microbial agents such as triclosan, cephalosporins, aminoglycosides, nitrofurantoin, silver ions, compounds, or salts; biofilm synthesis inhibitors such as nonsteroidal anti-inflammatory agents and chelating agents such as ethylenediaminetetraacetic acid, O,O'-bis(2-aminoethyl) ethyleneglycol-N,N,N',N'-tetraacetic acid and mixtures thereof, antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins (MCP-1) and bone morphogenic proteins ("BMP's"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMP's are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin⁻) cells including Lin⁻CD34⁻, Lin⁻CD34⁺, Lin⁻cKit⁺, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating to be applied to a medical device or applied onto a polymeric coating on a medical device. The polymers of the polymeric coatings may be biodegradable or non-biodegradable. Non-limiting examples of suitable non-biodegradable polymers include polystyrene; polystyrene maleic anhydride; polyisobutylene copolymers such as styrene-isobutylene-styrene block copolymers (SIBS) and styrene-ethylene/butylene-styrene (SEBS) block copolymers; polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides including poly(methylmethacrylate-butylacetate-methylmethacrylate) block copolymers; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one of skill in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, pacemakers, electrodes, leads, defibrillators, joint and bone implants, spinal implants, access ports, intra-aortic balloon pumps, heart valves, sutures, artificial hearts, neurological stimulators, cochlear implants, retinal implants, and other devices that can be used in connection with therapeutic coatings. Such medical devices are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The foregoing description and examples have been set forth merely to illustrate the invention and are not intended as being limiting. Each of the disclosed aspects and embodiments may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A system for coating a medical device comprising: a medical device support to hold a medical device; and a deposition system comprising: a microdrop source to generate at least one microdrop of a coating material, the microdrop source having a reservoir to contain coating material and an outlet to eject the microdrop; a charging electrode; and a control electrode adapted to generate a field between the microdrop source and the support; wherein the microdrop source ejects the microdrop from the outlet along an initial trajectory; and wherein the field generated by the control electrode alters the initial trajectory of the microdrop, wherein the microdrop source is selected from the group consisting of an ink jet, thermal ink jet, piezoelectric direct pressure pulse, acoustically disrupted continuous fluid jet, and focused acoustic beam ejection.

2. The system of claim 1, wherein the coating material comprises a therapeutic agent.

3. The system of claim 1, wherein the charging electrode electrically charges the microdrop generated by the microdrop source.

4. The system of claim 1, wherein the charging electrode electrically charges coating material in the reservoir.

5. The system of claim 1, wherein the microdrop source generates a plurality of microdrops of the coating material at a constant frequency.

6. The system of claim 1, wherein the deposition system further comprises a waste tray disposed between the microdrop source and the support.

7. The system of claim 1, further comprising a scanner to scan the medical device.

8. The system of claim 7, further comprising a control system, wherein the scanner communicates with the control system.

9. The system of claim 8, wherein the control system controls the position of at least one of the deposition system and the support.

10. The system of claim 9, wherein the control system controls the position of the deposition system relative to the support by translating the deposition system in a direction along an axis of the medical device.

11. The system of claim 9, wherein the control system controls the position of the deposition system relative to the support by rotating the deposition system in a direction around a circumference of the medical device.

12. The system of claim 9, wherein the control system controls the position of the support relative to the deposition system by translating the support in a direction along an axis of the medical device.

13. The system of claim 9, wherein the control system controls the position of the support relative to the deposition system by rotating the support.

14. The system of claim 8, wherein the control system controls the generation of microdrops deposited on the medical device.

15. The system of claim 8, wherein the control system controls the field generated by the control electrode.

16. The system of claim 1, wherein the control electrode comprises an electrode array.

17. The system of claim 1, wherein the control electrode generates an electric field.

18. The system of claim 1, wherein the control electrode generates a magnetic field.

19. The system of claim 1, wherein the field is adjustable.

20. The system of claim 1, wherein the medical device is a stent.

21. A system for coating a medical device comprising:
a medical device support to hold a medical device;
a deposition system comprising:
a microdrop source to generate a plurality of microdrops of a coating material, the coating material comprising a therapeutic agent, the microdrop source being selected from the group consisting of an ink jet, thermal ink jet, piezoelectric direct pressure pulse, acoustically disrupted continuous fluid jet, and focused acoustic beam ejection;
a charging electrode; and
a control electrode adapted to generate a field between the microdrop source and the support;
a control system to control the position of at least one of the medical device support and the deposition system; and
a scanning system to communicate with the control system; wherein the microdrop source ejects microdrops from an outlet of the microdrop source towards the medical device along an initial trajectory; wherein the microdrop source generates microdrops at a constant frequency; and wherein the field generated by the control electrode alters the initial trajectory of the microdrops.

22. The system of claim 21 wherein the control system controls the field generated by the control electrode.

* * * * *